United States Patent [19]

Atwal

[11] Patent Number: 4,684,655
[45] Date of Patent: Aug. 4, 1987

[54] 1,2,3,4-TETRAHYDRO-6-SUBSTITUTED-4-ARYL-3-SUBSTITUTED-2-THIOXO(OR OXO)-5-PYRIMIDINECARBOXYLIC ACIDS AND ESTERS AND USE THEREOF TO LOWER BLOOD PRESSURE

[75] Inventor: Karnail Atwal, Cranbury, N.J.

[73] Assignee: E. R. Squibb & Sons, Inc., Princeton, N.J.

[21] Appl. No.: 839,770

[22] Filed: Mar. 14, 1986

[51] Int. Cl.[4] .................. A61K 31/505; C07D 239/22
[52] U.S. Cl. .................................... 514/274; 544/316; 544/318
[58] Field of Search .................. 544/316, 318; 514/274

[56] References Cited

U.S. PATENT DOCUMENTS

| 4,532,248 | 7/1985 | Franckwiak et al. | 514/302 |
| 4,609,494 | 9/1986 | Baldwin et al. | 544/250 |

FOREIGN PATENT DOCUMENTS

| 0157219 | 10/1985 | European Pat. Off. | 514/274 |
| 3234684 | 3/1984 | Fed. Rep. of Germany | 544/316 |
| 868030 | 5/1961 | United Kingdom | 544/316 |
| 838030 | 5/1961 | United Kingdom | 514/274 |

OTHER PUBLICATIONS

*Medicinal Chemistry,* Burger Edit, 2nd Ed., 1960, pp. 565–571, 579–581, 600, and 601.
Khanina et al., Khim. Farm Zh., vol. 12, pp. 1321–1322 (1978) "Synthesis and Pharmacological Investigation . . . ".
Konyukhov et al., Zh. Organ. Khim., vol. 1, No. 8, pp. 1487–1489 (1965), "Synthesis and Investigation . . . ".
Elkasaby, Pakistan J.Sci.Ind.Res., vol. 21, No. 2, pp. 58–61 (1978), "Condensation of Ethyl α-Acetylcinnametes with Thioureas".
George et al., Synthesis (1975) pp. 405–407, "Condensed Heterocycles from 5-Ethoxycarbonyl-6-Methyltetrahydropyrimidin-2-Ones".
Folkers et al., J.Am.Chem.Soc., vol. 56, pp. 1374–1377 (1934), "Researches on Pyrimidines . . . ".
J. Org. Chem., vol. 50, pp. 4227–4230, "Synthesis of Novel Dihydropyrimidines and Tetrahydropyrimidines", Cho et al.(1985).
Chemical Abstracts, 1955:14769I, "Synthesis of Some 2-Oxo-4-Aryl-5-Carbethoxy-6-Trifluoromethyl-1,2,3,4-Tetrahydropyrimidines", Rutter et al.
Chemical Abstracts 1944:2653(4), "Synthesis of the Ethyl Esters of Some 2-Oxo-2-Thio-1,2,3,4-Tetrahydro-5-Pyrimidinecarboxylic Acids", McKinstry.
Chemical Abstracts 1944:4318(4), "The Chemotherapy of Experimental Virus Infections", McKinstry et al.

*Primary Examiner*—Henry R. Jiles
*Assistant Examiner*—Kurt G. Briscoe
*Attorney, Agent, or Firm*—Lawrence S. Levinson; Donald J. Barrack

[57] ABSTRACT

Cardiovascular activity is exhibited by compounds having the formula

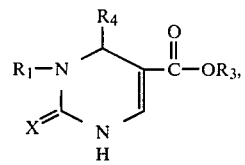

and pharmaceutically acceptable salts thereof wherein
X is oxygen or sulfur;
$R_1$ is alkyl, cycloalkyl, alkenyl, alkynyl, aryl —$(CH_2)_n$—$Y_2$, —$(CH_2)_p$—$Y_3$ or halo substituted alkyl;
$R_2$ is hydrogen, alkyl, alkenyl, alkynyl, cycloalkyl, aryl, —$(CH_2)_n$—$Y_1$, or halo substituted alkyl;
$R_3$ is hydrogen, alkyl, cycloalkyl, aryl, heterocyclo, —$(CH_2)_n$—$Y_2$, —$(CH_2)_p$—$Y_3$, or halo substituted alkyl;
$R_4$ is aryl or heterocyclo;
$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl

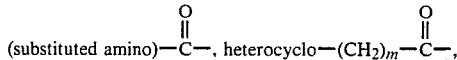

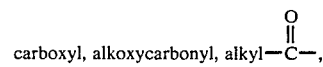

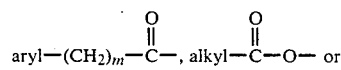

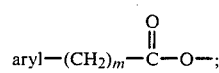

$Y_2$ is cycloalkyl, aryl, heterocyclo, carbamoyl,

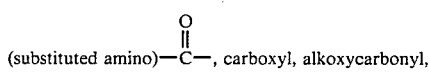

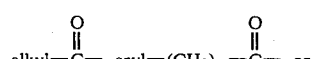

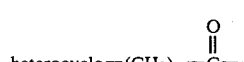

$Y_3$ is hydroxyl, alkoxy, aryl—$(CH_2)_m$—O—, mercapto, alkylthio, aryl—$(CH_2)_m$—S—,

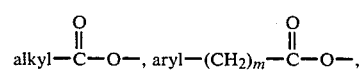

amino, or substituted amino;
m is 0 or an integer of 1 to 6;
n is an integer of 1 to 6; and
p is an integer of 2 to 6.

21 Claims, No Drawings

1,2,3,4-TETRAHYDRO-6-SUBSTITUTED-4-ARYL-3-SUBSTITUTED-2-THIOXO(OR OXO)-5-PYRIMIDINECARBOXYLIC ACIDS AND ESTERS AND USE THEREOF TO LOWER BLOOD PRESSURE

BRIEF DESCRIPTION OF THE INVENTION

Compounds having the formula

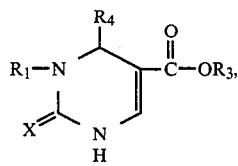

and pharmaceutically acceptable salts thereof, are cardiovascular agents. In formula I, and throughout the specification, the symbols are as defined below.

X is oxygen or sulfur;

$R_1$ is alkyl, cycloalkyl, alkenyl, alkynyl, aryl, —$(CH_2)_n$—$Y_2$, —$(CH_2)_p$—$Y_3$ or halo substituted alkyl;

$R_2$ is hydrogen, alkyl, alkenyl, alkynyl, cycloalkyl, aryl, —$(CH_2)_n$—$Y_1$, or halo substituted alkyl;

$R_3$ is hydrogen, alkyl, cycloalkyl, aryl, heterocyclo, —$(CH_2)_n$—$Y_2$, —$(CH_2)_p$—$Y_3$, or halo substituted alkyl;

$R_4$ is aryl or heterocyclo;

$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl,

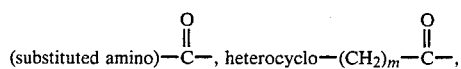

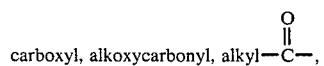

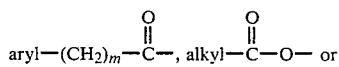

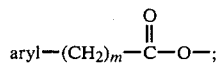

$Y_2$ is cycloalkyl, aryl, heterocyclo, carbamoyl,

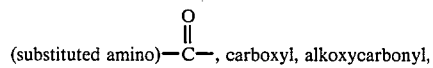

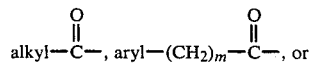

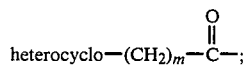

$Y_3$ is hydroxyl, alkoxy, aryl—$(CH_2)_m$—O—, mercapto, alkylthio, aryl—$(CH_2)_m$—S—,

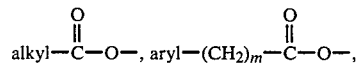

amino, or substituted amino;

m is 0 or an integer of 1 to 6;

n is an integer of 1 to 6; and p is an integer of 2 to 6.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkyoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, which is preferred, pentafluoroethyl, 2,2,2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "heterocyclo" refers to fully saturated or unsaturated rings of 5 or 6 atoms containing one or two oxygen or sulfur atoms and/or one to four nitrogen atoms provided that the total number of hetero atoms in the ring is 4 or less. The heterocyclo ring is attached by way of an available carbon atom. Preferred monocyclic heterocyclo groups include 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, and 2-, 3- and 4-azepinyl. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings as defined above substituted with one, or more, alkyl, arylalkyl, diarylalkyl, alkylthio, alkoxy, halo, nitro, oxo, cyano, hydroxy, amino, alkylamino, dialkylamino, trifluoromethyl, isocyanato, isothiocyanato or difluoromethoxy groups.

The term "substituted amino" refers to a group of the formula —$NZ_1Z_2$ wherein $Z_1$ is hydrogen, alkyl, or aryl—$(CH_2)_m$—and $Z_2$ is alkyl or aryl—$(CH_2)_m$—or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

DETAILED DESCRIPTION OF THE INVENTION

The compounds of formula I, and the pharmaceutically acceptable salts thereof, are cardiovascular agents. They act as calcium entry blocking vasodilators and are especially useful as hypotensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, it is believed that such compounds in addition to being hypotensive agents may also be useful as antiarrhythmic agents, anti-anginal agents, anti-fibrillatory agents, anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is sulfur can be prepared by reacting a keto ester compound having the formula

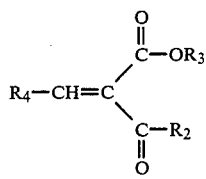
II with an S-(phenylmethyl)thiopseudourea having the formula

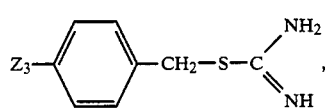
III or a salt thereof. In formula III, and throughout the specification, $Z_3$ is hydrogen or methoxy. The reaction mixture is heated in the presence of sodium acetate to yield a tautomeric mixture of compounds having the formulas

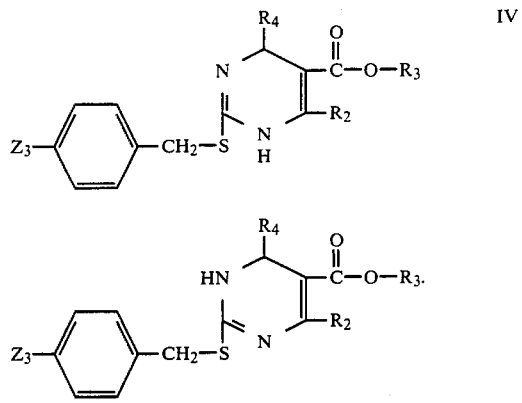
IV

Reaction of a tautomeric mixture of formula IV with a compound having the formula $R_1$—halogen (V)

in the presence of an inorganic base yields the corresponding compound having the formula

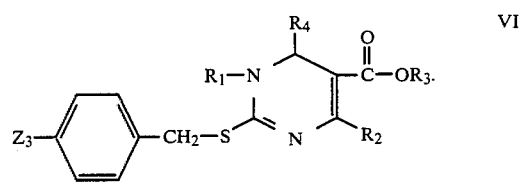
VI

A compound of formula VI wherein $Z_3$ is hydrogen can be converted to the corresponding product of formula I wherein X is sulfur by treatment with bromotrimethylsilane. A compound of formula VI wherein $Z_3$ is methoxy can be converted to the corresponding product of formula I wherein X is sulfur by treatment with trifluoroacetic acid and ethanethiol.

The compounds of formula I wherein X is oxygen can be prepared by heating a keto ester of formula II with

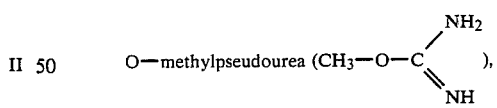

or a salt thereof, in the presence of sodium acetate or sodium bicarbonate to yield a tautomeric mixture of compounds having the formulas

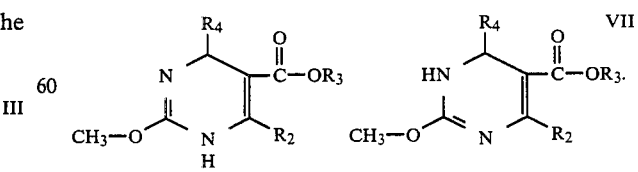
VII

Reaction of a tautomeric mixture of formula VII with a compound of formula V in the presence of an inorganic base yields the corresponding compound having the formula

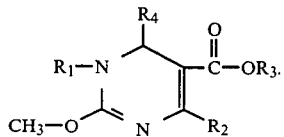

A compound of formula VIII can be converted to the corresponding product of forumula I wherein X is oxygen by treatment with hydrochloric acid.

In those instances wherein the reactants described above contain reactive substituents not meant to participate in the reaction, it may be necessary to first protect these functional groups, carry out the desired reaction, and then remove the protecting group.

The compounds of formula I that contain a basic or acid group form acid addition and basic salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g., sodium, potassium and lithium) and alkaline earth metal salts (e.g., calcium and magnesium). The salts can be obtained by reacting the product with an equivalent amount of the acid in a medium in which the salt precipitates.

Preferred compounds of this invention are those wherein:

$R_2$ is alkyl (especially methyl), $R_3$ is alkyl (especially ethyl) and $R_4$ is 3-nitrophenyl.

The following examples are specific embodiments of this invention.

EXAMPLE 1

1,2,3,4-Tetrahydro-6-methyl-4-(3-nitrophenyl)-2-oxo-3-(3-phenylpropyl)-5-pyrimidinecarboxylic acid, 1-methylethyl ester (A)

1,4-Dihydro-2-methoxy-6-methyl-4-(3-nitrophenyl)-5-pyrimidinecarboxylic acid, 1-methylethyl ester A reaction mixture containing 2-[(3-nitrophenyl)methylene]-3-oxobutanoic acid, 1-methylethyl ester (10.0 g, 36.0 mmol), sodium bicarbonate (8.40 g, 108 mmol), and O-methylpseudourea hydrogen sulfate (8.06 g, 46.8 mmol) in dimethylformamide (54 ml) was heated at 60° C. under argon for about 2½ days. The reaction mixture was diluted with water and extracted with ethyl acetate. The organic phase was washed with water (six times) and saturated sodium chloride, dried (potassium carbonate) and evaporated. The residue was pressed through a short pad of silica gel and crystallized from isopropyl ether/hexanes to give the title compound as yellow crystals (8.04 g).

(B)

1,6-Dihydro-2-methoxy-6-methyl-4-(3-nitrophenyl)-1-(3-phenylpropyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (4.0 g, 12.0 mmol) in dry dimethylformamide (10 ml) under argon was treated with finely ground potassium carbonate (4.97 g, 36.0 mmoles), 3-phenylpropyl bromide (2.19 ml, 14.4 mmoles) and a catalytic amount of 18-crown-6. The resulting suspension was allowed to stir at room temperature for 72 hours, diluted with ether, filtered and the filtrate washed with water and brine. After drying over anhydrous magnesium sulfate, the solvent was evaporated. The residue was purified by flash chromatography (10–15% ethyl acetate in hexanes) to provide the desired product (3.29 g) as a yellow oil.

(C)

1,2,3,4-Tetrahydro-6-methyl-4-(3-nitrophenyl)-2-oxo-3-(3-phenylpropyl)-5-pyrimidinecarboxylic acid, 1-methylethyl ester A solution of 1,6-dihydro-2-methoxy-6-methyl-4-(3-nitrophenyl)-1-(3-phenylpropyl)-5-pyrimidinecarboxylic acid, 1-methylethyl ester (1.96 g. 4.34 mmoles) in methanol (20 ml) was treated with 2.5 N hydrochloric acid (5 ml) and the resulting mixture was allowed to stir at room temperature overnight. A colorless solid precipitated out. Methanol was evaporated and the residue was taken up in ethyl acetate. The solution was washed with water, sodium bicarbonate solution and brine. It was dried over anhydrous magnesium sulfate and evaporated. The residue was crystallized from dichloromethane/isopropyl ether to provide the title compound as a colorless solid (1.61 g), melting point 149.5-151.5° C.

Analysis Calc'd. for $C_{24}H_{27}N_3O_5$:

C, 65.89; H, 6.22; N, 9.60.

Found: C, 66.05; H, 6.28; N, 9.60.

EXAMPLE 2

1,2,3,4-Tetrahydro-6-methyl-4-(3-nitrophenyl)-2-oxo-3-(2-propenyl)-5-pyrimidinecarboxylic acid, 1-methylethyl ester (A)

1,6-Dihydro-2-methoxy-6-methyl-4-(3-nitrophenyl)-1-(2-propenyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (4.0 g, 12.0 mmol; see Example 1A) in dry dimethylformamide (10 ml) was treated with finely ground potassium carbonate (6.6 g, 48.0 mmoles) and allyl bromide (1.7 ml, 20.0 mmole). The resulting suspension was allowed to stir under argon at room temperature for 10 hours. The reaction was diluted with ethyl acetate, filtered and the filtrate was washed with water and brine. It was dried over anhydrous magnesium sulfate and evaporated to provide a yellow oil. Purification by flash chromatography (20% ethyl acetate in hexanes) yielded the title compound (2.64 g) as yellow oil.

(B)

1,2,3,4-Tetrahydro-6-methyl-4-(3-nitrophenyl)-2-oxo-3-(2-propenyl)-5-pyrimidinecarboxylic acid, 1-methylethyl ester A solution of 1,6-dihydro-2-methoxy-6-methyl-4-(3-nitrophenyl)-1-(2-propenyl)-5-pyrimidine carboxylic acid, 1-methylethyl ester (1.44 g, 3.86 mmol) in methanol (10 ml) was treated with 2.5 N hydrochloric acid (30 ml) and the reaction was allowed to stir at room temperature for 10 hours. By the end of this period, a colorless precipitate was formed. The reaction was diluted with ethyl acetate and the organic layer was separated. The aqueous layer was reextracted with ethyl acetate and the combined organic extracts were washed with sodium bicarbonate and brine. After drying over anydrous magnesium sulfate, the solvent was evaporated to provide a colorless solid. It was triturated with isopropyl ester and was filtered (1.07 g). Recrystallization from dichloromethane-isopropyl ether gave the title compound (975 mg) as a colorless solid, melting point 172°–174° C.

Analysis Calc'd for $C_{18}H_{21}N_3O_5$:
C, 60.16; H, 5.89; N 11.69.
Found: C, 60.08; H 5.83; N, 11.65.

EXAMPLE 3

1,2,3,4-Tetrahydro-6-methyl-3-[3-[methyl(phenylmethyl)amino]propyl]-4-(3-nitrophenyl)-2-oxo-5-pyrimidinecarboxylic acid, 1-methylethyl ester, monohydrochloride (A) N-Benzyl-3-chloro-N-methylpropylamine A solution of N-benzyl-N-methylpropanol 25.0 g, 139.5 mmol) in chloroform (50 ml) was cooled in an ice bath and was treated dropwise with methanolic hydrochloric acid (150 ml of a 1N solution). After the addition was finished, the cooling bath was removed, and the solution was allowed to warm to room temperature. The solvent and excess hydrochloric acid were removed under reduced pressure to yield a thick oil. This was dissolved in chloroform (25 ml), cooled to 0° C. and was treated dropwise with thionyl chloride (30 ml). After the addition was complete, the reaction was allowed to warm to room temperature and then heated at 70° C. for 3 hours. The reaction was allowed to cool to ambient temperature and the solvent was removed in vacuo. The residue was partitioned between ether/chloroform (80:20) and 2N sodium hydroxide. The organic layer was separated and the aqueous layer was reextracted with the same solvent system. The combined extracts were washed with brine, dried over anhydrous magnesium sulfate and evaporated to provide a yellow oil (26.1 g).

(B)
1,6-Dihydro-2-methoxy-6-methyl-1-[3-[methyl(phenylmethyl)amino]propyl]-4-(3-nitrophenyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methyethyl ester (2.0 g, 6.0 mmol) in dimethylformamide (7.0 ml) was treated with finely ground potassium carbonate (1.7 g, 12.0 mmoles), N-benzyl-3-chloro-N-methylpropylamine (2.37 g, 12.0 mmol) and a catalytic amount of 18-crown-6. The reaction was heated at 70°–75° C. under argon overnight. The reaction was allowed to cool down to room temperature and was diluted with ether. It was filtered, and the filtrate was washed with water, brine and was dried over anhydrous magnesium sulfate. Evaporation of solvent provided a brown oil which was purified by flash chromatography (20% acetone in hexanes) to yield the title compound (1.51 g) as a yellow oil.

(C)
1,2,3,4-Tetrahydro-6-methyl-3-[3-[methyl(phenylmethyl)amino]propyl]-4-(3-nitrophenyl)-2-oxo-5-pyrimidinecarboxylic acid, 1-methylethyl ester, monohydrochloride A solution of 1,6-dihydro-2-methoxy-6-methyl-1-[3 -[methyl(phenylmethyl)amino]propyl]-4-(3-nitrophenyl)- 5-pyrimidinecarboxylic acid, 1-methylethyl ester (1.50 g, 3.0 mmol) in methanol (12.0 ml) was treated with 2.5 N hydrochloric acid (5.0 ml). The reaction was allowed to stir at room temperature for 16 hours. The solvent was evaporated and the residue was treated with sodium hydroxide and extracted with dichloromethane. The combined extracts were washed with brine and dried over anhydrous magnesium sulfate. The solvent was evaporated and the residue in dichloromethane was converted into the hydrochloric acid salt. The solvent was removed and the residue was crystallized from acetonitrile-ether to provide colorless solid (1.2 g). Recrystallization from the same solvent system provided the analytically pure title compound (1.08 g), melting point 165°–170° C.

Analysis Calc'd. for $C_{26}H_{32}N_4O_5 \cdot HCl$:
C, 60.40; H, 6.43; N, 10.83; Cl, 6.86.
Found: C, 60.16; H, 6.39; N, 10.79; Cl, 6.78.

EXAMPLE 4

1,2,3,4-Tetrahydro-6-methyl-4-(3-nitrophenyl)-3-(2-propenyl) -2-thioxo-5-pyrimidinecarboxylic acid, methyl ester (A) S-(4-Methoxybenzyl)thiopseudourea, hydrochloride A suspension of thiourea (38 g, 50.0 mmole) in dry tetrahydrofuran (40 ml) was cooled to 0° C. under argon and was treated dropwise with 4-methoxybenzylchloride (8.0 g, 50.0 mmole). After the addition was completed, the cooling bath was removed and the reaction was allowed to stir at room temperature for 2 hours. It was then heated at 60°–65° C. for 4 hours whereupon a colorless voluminous precipitate was formed. The reaction was allowed to cool down to room temperature and was diluted with anhydrous ether. The solid was filtered off and washed with anhydrous ether to give 10.92 g of 2-(4-methoxybenzyl)-2-thiopseudourea, hydrochloride, melting point 161°–163.5° C.

Analysis Calc'd. for $C_9H_{12}N_2OS \cdot HCl$: C, 46.45; H, 5.63; N, 12.04; S, 13.78; Cl, 15.23.
Found: C, 46.48; H, 5.64; N, 12.25; S, 13.74; Cl, 15.31.

(B)
1,4-Dihydro-2-[[(4-methoxyphenyl)methyl]thio]-6-methyl-4-(3-nitrophenyl)-5-pyrimidinecarboxylic acid, methyl ester A solution of 2-[(3-nitrophenyl)methylene]-3-oxobutanoic acid, methyl ester (5.0 g, 0.02 mole) in 20 ml of dimethylformamide under argon at room temperature was treated with S-(4-methoxybenzyl)-S-thiopseudourea, hydrochloride (4.65 g, 0.02 mole) and sodium acetate (1.64 g, 0.02 mole). The mixture was then heated at 65°±5° C. for 3 hours. Upon cooling, ethyl acetate was added and a small amount of solids were filtered. The filtrate was washed with water (twice), aqueous sodium bicarbonate and saturated brine. The aqueous washes were extracted with fresh ethyl acetate. The combined filtrate and washings were dried (magnesium sulfate) and concentrated in vacuo to give about 9 g of crude product. Crystallization from acetone-isopropyl ether gave 6.8 g of product, melting point 125°–127.5° C., tlc, silica gel, ethyl acetate/hexane (1:1), $R_f = 0.48$.

Analysis Calc'd. for $C_{21}H_{21}N_3O_5S$: C, 59.00; H, 4.95; N, 9.83; S, 7.50.

Found: C, 58.86; H, 4.82; N, 9.51; S, 7.25.

(C)
1,6-Dihydro-2-[[(4-methoxyphenyl)methyl]thio]-4-methyl-6-(3-nitrophenyl)-1-(2-propenyl)-5-pyrimidinecarboxylic acid, methyl ester A slurry of sodium hydride (168 mg, 4.2 mmole, 60% in mineral oil dispersion) in 5 ml of dry tetrahydrofuran at 0° C. under argon was treated dropwise with 1,4-dihydro-2-[[(4-methoxyphenyl)methyl]thio]-6-methyl-4-(3-nitrophenyl)-5-pyrimidinecarboxylic acid, methylester in 15 ml of dry tetrahydrofuran. After an additional 10 minutes at 0° C., allyl bromide was added and the reaction mixture was allowed to warm to room temperature overnight.

Tetrahydrofuran was removed in vacuo and the residue, dissolved in ethyl acetate, was washed with 1N hydrochoric acid, water (twice), aqueous sodium bicarbonate, water and saturated brine. The aqueous fractions were extracted with fresh ethyl acetate. The combined organic fractions were dried (magnesium sulfate) and concentrated in vacuo to give 1.5 g of crude oily product. Flash chromatography on 250 ml of silica gel and elution with ethyl acetate/hexanes (1:4) gave 1.0 g of the title compound as an oil.

(D)
1,2,3,4-Tetrahydro-6-methyl-4-(3-nitrophenyl)-3-(2-propenyl)-2-thioxo-5-pyrimidinecarboxylic acid, methyl ester 1,6-Dihydro-2-[[(4-methoxyphenyl)methyl]thio]-4-methyl-6-(3-nitrophenyl)-1-(2-propenyl)-5-pyrimidinecarboxylic acid, methyl ester (1.0 g, 2.14 mmol) in 15 ml of dichloromethane under argon at room temperature was treated with trifluoroacetic acid (0.6 ml, 0.85 g, 7.7 mmole) and ethanethiol (0.4 ml, 0.33 g, 5.4 mmole). No change (tlc) occurred within 2 hours. Heating at reflux temperature, however, effected complete reaction in several hours.

Volatiles were evaporated in vacuo and the residue (solified) was triturated with isopropyl ether to give 0.65 g of off-white powder, melting point 171.5°–173.0° C. Crystallization from acetone/isopropyl ether afforded 450 mg of the title compound, melting point 175°–177° C.

Analysis Calc'd. for $C_{16}H_{17}N_3O_4S$:
C, 55.33; H, 4.94; N, 12.10; S, 9.23.
Found: C, 55.36; H, 4.95; N, 12.23; S, 9.11.

EXAMPLE 5
1,2,3,4-Tetrahydro-6-methyl-4-(3-nitrophenyl)-3-(2-propenyl)-2-thioxo-5-pyrimdinecarboxylic acid, ethyl ester

(A)
1,4-Dihydro-2-[[(4-methoxyphenyl)methyl]-thio]-6-methyl-4-(3-nitrophenyl)-5-pyrimidinecarboxylic acid, ethyl ester A mixture of 13.58 g of 2-(3-nitrophenyl)methylene]-3-oxobutanoic acid, ethyl ester, 12.0 g of S-[(4-methoxyphenyl)methyl]thiopseudourea, hydrochloride and 4.18 g (0.051 mole) of sodium acetate in 90 ml of dimethylformamide was stirred and heated at 70° C. for 4 hours. After cooling, ether was added followed by washing with water, sodium bicarbonate and brine. The dried solution was evaporated to give an oil which was treated with isopropyl ether to form 18.8 g of a cream colored solid, melting point 95°–97° C.

(B) 1,6-Dihydro-2-[[(4-methoxyphenyl)methyl]thio]-4-methyl-6-(3-nitrophenyl)-1-(2-propenyl)-5-pyrimidinecarboxylic acid, ethyl ester A stirred suspension of 0.26 g (0.0054 mmole) of sodium hydride (50%) in 15 ml of tetrahydrofuran (0°-5° C.) was treated slowly with a solution of 2.0 g of 1,6-dihydro-2-[[(4-methoxyphenyl)methyl]thio]-4-methyl-6-(3-nitrophenyl)-1-(2-propenyl)-5-pyrimidinecarboxylic acid, ethyl ester in 15 ml of tetrahydrofuran. After stirring for 10 minutes, 0.73 g (0.0060 mole) of allyl bromide was added and the mixture was stirred at room temperature overnight.

Ethyl acetate was added and the mixture was washed with 1N hydrochloric acid, sodium bicarbonate and brine. The dried solution was evaporated to give 2.3 g of an oil. Flash chromatography using dichloromethane gave 1.4 g of a yellow oil.

(C)
1,2,3,4-Tetrahydro-6-methyl-4-(3-nitrophenyl)-3-(2-propenyl)-2-thioxo-5-pyrimdinecarboxylic acid, ethyl ester A solution of 1.3 g (0.0027 mole) of 1,6- dihydro-2-[[(4-methoxyphenyl)methyl]thio]-4-methyl-6-(3-nitrophenyl)-1-(2-propenyl)-5-pyrimidinecarboxylic acid, ethyl ester in 20 ml of dichloromethane was treated with 1.0 ml (0.0130 mole) of trifluoroacetic acid and 0.4 g (0.0061 mole) of ethanethiol. After stirring overnight, the solvent was evaporated and the solid residue was triturated with ether to give 0.80 g of a cream colored solid, melting point 144°–146° C. Flash chromatography using ethyl acetate/hexane (1:3) gave 0.42 g of the title compound, melting point 154°–156° C.

Analysis Calc'd. for $C_{17}H_{19}N_3O_4S$:
C, 56.49; H, 5.29; N, 11.62; S, 8.87.
Found: C, 56.27; H, 5.31; N, 11.73; S, 8.85.

Additional compounds falling within the scope of this invention are:

4-(2,3-dichlorophenyl)-1,2,3,4-tetrahydro-6-methyl-3-[3-[(methyl)(phenylmethyl)amino]propyl]-2-oxo-5-pyrimidinecarboxylic acid, ethyl ester 1,2,3,4-tetrahydro-6-methyl-4-(2-nitrophenyl)-12-oxo-3-propyl-5-pyrimidinecarboxylic acid, 1-phenylmethyl-4-piperidinyl ester 1,2,3,4-tetrahydro-3,6-dimethyl-4-(3-nitrophenyl)-2-oxo-5-pyrimidinecarboxylic acid, 1-methylethyl ester 1,2,3,4-tetrahydro-6-methyl-3-[4-(dimethylamino)butyl]-2-oxo-4-[2-(trifluoromethyl)phenyl]-5-pyrimidinecarboxylic acid, ethyl ester 4-(7-benzofurazanyl)-1,2,3,4-tetrahydro-6-methyl-2-oxo-3-(2-propenyl)-5-pyrimidinecarboxylic acid, 2-[(methyl)(phenylmethyl)amino]ethyl ester 1,2,3,4-tetrahydro-6-methyl-4-[2-(methylthio)-3-pyridinyl]-2-oxo-3-[4-(4-pyrimidinyl)butyl]-5-pyrimidinecarboxylic acid, ethyl ester 4-(2-chloro-3-nitrophenyl)-1,2,3,4-tetrahydro-6-methyl-2-oxo-3-[3-[4-(phenylmethyl)-1-piperazinyl]propyl]-5-pyrimidinecarboxylic acid, ethyl ester 1,2,3,4-tetrahydro-6-methyl-4-(3-nitrophenyl)-2-oxo-3-[2-[4-(diphenylmethyl)-1-piperazinyl]ethyl]-5-pyrimidinecarboxylic acid, ethyl ester 4-(2-chlorophenyl)-1,2,3,4-tetrahydro-6-methyl-2-oxo-3-(2-propenyl)-5-pyrimidinecarboxylic acid, 2-[4-(phenylmethyl)-1-piperazinyl]ethyl ester 1,2,3,4-tetrahydro-6-methyl-4-(3-nitrophenyl)-2-oxo-3-(3-phenylpropyl)-5-pyrimidinecarboxylic acid, 2-[4-(diphenylmethyl)-1-piperazinyl]ethyl ester 4-(2,3-dichlorophenyl)-1,2,3,4-tetrahydro-6-methyl -3-[3-[(methyl)(phenylmethyl)amino]propyl]2-thioxo-5-pyrimidinecarboxylic acid, ethyl ester 1,2,3,4-tetrahydro-6-methyl-4-(2-nitrophenyl)-3-propyl-2-thioxo-5-pyrimidinecarboxylic acid, 1-phenylmethyl-4-piperidinyl ester 1,2,3,4-tetrahydro-3,6-dimethyl-4-(3-nitrophenyl)-2-thioxo-5-pyrimidinecarboxylic acid, 1-methylethyl ester 1,2,3,4-tetrahydro-6-methyl-3-[4-(dimethylamino)-butyl]-2-thioxo-4-[2-(trifluoromethyl)phenyl]-5-pyrimidinecarboxylic acid, ethyl ester 4-(7-benzofurazanyl)-1,2,3,4-tetrahydro-6-methyl -3-(2-propenyl)-2-thioxo-5-pyrimidinecarboxylic acid, 2-[(methyl)(phenylmethyl)amino]ethyl ester 1,2,3,4-tetrahydro-6-methyl-4-[2-(methylthio)-3-pyridinyl]-3-[4-(4-pyridinyl)butyl]-2-thioxo-5pyrimidinecarboxylic acid, ethyl ester 4-(2-chloro-3-nitrophenyl)-1,2,3,4-tetrahydro-6-methyl-3-[3-[4-(phenylmethyl)-1-piperazinyl]propyl]-2-thioxo-5-pyrimidinecarboxylic acid, ethyl ester 1,2,3,4-tetrahydro-6-methyl-4-(3-nitrophenyl)-3-[2-[4-(diphenylmethyl)-1-piperazinyl]ethyl]]-2-thioxo -5-pyrimidinecarboxylic acid, ethyl ester 4-(2-chlorophenyl)-1,2,3,4-tetrahydro-6-methyl-3-(2-propenyl)-2-thioxo-5-pyrimidinecarboxy acid, 2-[4-(phenylmethyl)-1-piperazinyl]ethyl ester 1,2,3,4-tetrahydro-6-methyl-4-(3-nitrophenyl)-3-(3-phenylpropyl)-2-thioxo-5-pyrimidinecarbo acid, 2-[4-(diphenylmethyl)-1-piperazinyl]ethyl ester

What is claimed is:

1. A compound having the formula

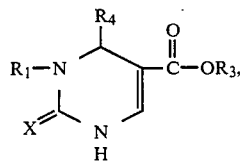

or a pharmaceutically acceptable salt thereof wherein
X is oxygen or sulfur;
$R_1$ is cycloalkyl, alkenyl, alkynyl, aryl, —$(CH_2)_n$—$Y_2$, —$(CH_2)_p$—$Y_3$ or halo substituted alkyl;
$R_2$ is hydrogen, alkyl, alkenyl, alkynyl, cycloalkyl, aryl, —$(CH_2)_n$—$Y_1$, or halo substituted alkyl;
$R_3$ is hydrogen, alkyl, cycloakyl, aryl, —$(CH_2)_n$—$Y_2$, —$(CH_2)_p$—$Y_3$, or halo substituted alkyl;
$R_4$ is aryl;
$Y_1$ is cycloalkyl, aryl, hydroxyl, alkoxy, aryl—$(CH_2)_m$—, O—, mercapto, alkylthio, aryl—$(CH_2)_m$—S—, amino, substituted amino, carbamoyl,

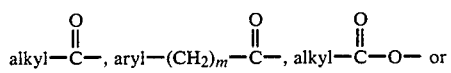

(substituted amino)—C—, carboxyl, alkoxycarbonyl, alkyl—C—, aryl—$(CH_2)_m$—C—, alkyl—C—O— or aryl—$(CH_2)_m$—C—O—;

$Y_2$ is cycloalkyl, aryl, carbamoyl, (substituted amino)—C—, carboxyl, alkoxycarbonyl, alkyl—C—, or aryl—$(CH_2)_m$—C—

$Y_3$ is hydroxyl, alkoxy, aryl—$(CH_2)_m$—O—, mercapto, alkylthio, aryl—$(CH_2)_m$—S—, alkyl—C—O—, aryl—$(CH_2)_m$—C—O—, amino, or substituted amino;
m is 0 or an integer of 1 to 6;
n is an integer of 1 to 6; and
p is an integer of 2 to 6; wherein
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
the term "substituted amino" refers to a group of the formula —$NZ_1Z_2$ wherein $Z_1$ is hydrogen, alkyl, or aryl—$(CH_2)_m$—and and $Z_2$ is alkyl or aryl—$(CH_2)_m$—;
the term "cycloalkyl" refers to a group having 3,4,5,6 or 7 carbon atoms.

2. A compound in accordance with claim 1 wherein X is oxygen.
3. A compound in accordance with claim 1 wherein X is sulfur.
4. A compound in accordance with claim 2 wherein $R_2$ is alkyl.
5. A compound in accordance with claim 3 wherein $R_2$ is alkyl.
6. A compound in accordance with claim 2 wherein $R_3$ is alkyl.
7. A compound in accordance with claim 3 wherein $R_3$ is alkyl.
8. A compound in accordance with claim 2 wherein $R_4$ is 3-nitrophenyl.
9. A compound in accordance with claim 3 wherein $R_4$ is 3-nitrophenyl.
10. A compound in accordance with claim 1 wherein $R_1$ is alkenyl.
11. A compound in accordance with claim 1 wherein $R_1$ is alkynyl.
12. A compound in accordance with claim 1 wherein $R_1$ is aryl.
13. A compound in accordance with claim 1 wherein $R_1$ is arylalkyl.
14. A compound in accordance with claim 1 wherein $R_1$ is —$(CH_2)_n$—$Y_2$ or —$(CH_2)_p$—$Y_3$.
15. A compound in accordance with claim 1 wherein X is sulfur, $R_2$ is methyl, $R_3$ is ethyl and $R_4$ is 3-nitrophenyl.
16. The compound in accordance with claim 1, 1,2,3,4-tetrahydro-6-methyl-4-(3-nitrophenyl)-2-oxo-3-(3-phenylpropyl) -5-pyrimidinecarboxylic acid, 1-methylethyl ester.
17. The compound in accordance with claim 1, 1,2,3,4-tetrahydro-6-methyl-4-(3-nitrophenyl)-2Oxo -3-(2-propenyl)-5-pyrimidinecarboxylic acid, 1-methylethyl ester.

18. The compound in accordance with claim 1, 1,2,3,4-tetrahydro-6-methyl-3-[3-[methyl(phenylmethyl)amino]propyl]-4-(3-nitrophenyl)-2-oxo-5-pyrimidinecarboxylic acid, 1-methylethyl ester, monohydrochloride.

19. The compound in accordance with claim 1, 1,2,3,4-tetrahydro-6-methyl-4-(3-nitrophenyl)-3-(2-propenyl)-2-thioxo-5-pyrimidinecarboxylic acid, methyl ester.

20. The compound in accordance with claim 1, 1,2,3,4-tetrahydro-6-methyl-4-(3-nitrophenyl)-3-(2-propenyl)-2-thioxo-5-pyrimdinecarboxylic acid, ethyl ester.

21. A method of lowering blood pressure in a mammalian host in need thereof, which comprises administering to said host an effective amount of a compound having the formula

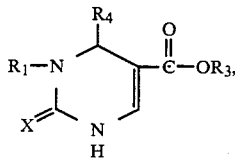

or a pharmaceutically acceptable salt thereof wherein
X is oxygen or sulfur;
$R_1$ is cycloalkyl, alkenyl, alkynyl, aryl, —$(CH_2)_n$—$Y_2$, —$(CH_2)_p$—$Y_3$ or halo substituted alkyl;
$R_2$ is hydrogen, alkyl, alkenyl, alkynyl, cycloalkyl, aryl, —$(CH_2)n$—$Y_1$, or halo substituted alkyl;
$R_3$ is hydrogen, alkyl, cycloalkyl, aryl, $(CH_2)n$—$Y_2$, —$(CH_2)p$—$Y_3$, or halo substituted alkyl;
$R_4$ is aryl;
$Y_1$ is cycloalkyl, aryl, hydroxyl, alkoxy, aryl—$(CH_2)_m$—O—, mercapto, alkylthio, aryl —$(CH_2)_m$—S—, amino, substituted amino, carbamoyl,

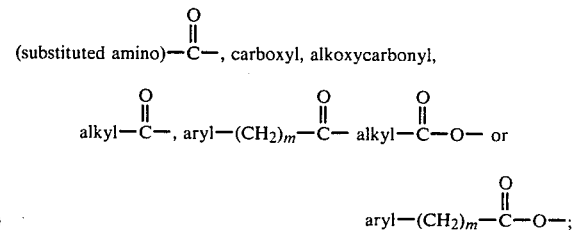

$Y_2$ is cycloalkyl, aryl, carbamoyl,

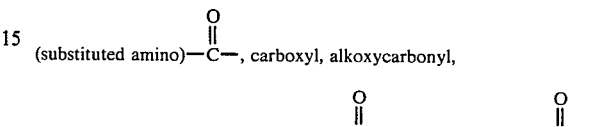

$Y_3$ is hydroxyl, alkoxy, aryl—$(CH_2)_m$—O—, mercapto, alkylthio, aryl—$(CH_2)_m$—S—,

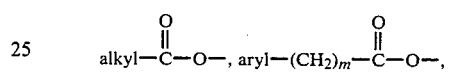

amino, or substituted amino;
m is 0 or an integer of 1 to 6;
n is an integer of 1 to 6; and
p is an integer of 2 to 6;
wherein the term "aryl" refers to phenyl or phenyl substituted with one, two or three alkyl, alkoxy, alklthio, halo, nitro, cyano, hydroxy, amino, alkyl amino, dialkylamino, trifluoromethyl, isothiocyanato, isocyanato, or difluoromethyoxy groups;
the term "substituted amino" refers to a group of the formula —$NZ_1Z_2$ wherein $Z_1$ is hydrogen, alkyl, or aryl—$(CH_2)_m$—amd $Z_2$ is alkyl or aryl—$(CH_2)_m$—; and the term "cycloalkyl" refers to a group having 3, 4, 5, 6 or 7 carbon atoms.

* * * * *

UNITED STATES PATENT AND TRADEMARK OFFICE
CERTIFICATE OF CORRECTION

PATENT NO. : 4,684,655
DATED : August 4, 1987
INVENTOR(S) : Karnail Atwal

It is certified that error appears in the above-identified patent and that said Letters Patent is hereby corrected as shown below:

In the Abstract; column 1, lines 11-17; claim 1; and claim 21; please amend the structure to read:

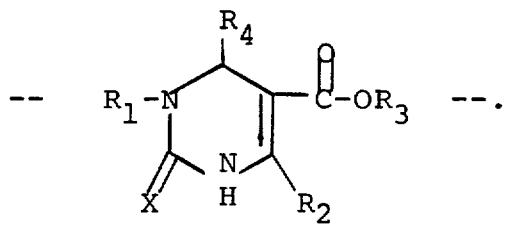

In column 10, line 45, "12-oxo" should read --2-oxo--.

In column 11, line 21, "5pyrimidinecarboxylic" should read --5-pyrimidinecarboxylic--.

UNITED STATES PATENT AND TRADEMARK OFFICE
CERTIFICATE OF CORRECTION

PATENT NO. : 4,684,655

DATED : August 4, 1987

INVENTOR(S) : Karnail Atwal

It is certified that error appears in the above-identified patent and that said Letters Patent is hereby corrected as shown below:

In claim 17, (column 12, line 66), "20xo" should read

--2-oxo--.

Signed and Sealed this

Fifth Day of April, 1988

Attest:

Attesting Officer

DONALD J. QUIGG

Commissioner of Patents and Trademarks